US00PP25611P2

(12) United States Plant Patent
Saul

(10) Patent No.: US PP25,611 P2
(45) Date of Patent: Jun. 2, 2015

(54) ***ANTIRRHINUM* PLANT NAMED 'SNAP DADDY PEACH'**

(50) Latin Name: *Antirrhinum majus*
Varietal Denomination: Snap Daddy Peach

(71) Applicant: Richard Gregg Saul, Cleveland, GA (US)

(72) Inventor: Richard Gregg Saul, Cleveland, GA (US)

(73) Assignee: Itsaul Plants LLC, Alpharetta, GA (US)

( * ) Notice: Subject to any disclaimer, the term of this patent is extended or adjusted under 35 U.S.C. 154(b) by 93 days.

(21) Appl. No.: 13/987,937

(22) Filed: Sep. 16, 2013

(51) Int. Cl.
*A01H 5/02* (2006.01)

(52) U.S. Cl.
USPC ..... Plt./322

(58) Field of Classification Search
USPC ..... Plt./322
CPC ..... A01H 5/02; A01H 5/00
See application file for complete search history.

*Primary Examiner* — Kent L Bell
(74) *Attorney, Agent, or Firm* — Penny J. Aguirre

(57) ABSTRACT

A new cultivar of *Antirrhinum*, 'Snap Daddy Peach', characterized by its variegated foliage with distinct yellow margins and soft, grey-green centers, its new foliage with margins that are a brighter yellow than the mature foliage, its full flower heads, its uniquely colored flowers that are a blend of pink, yellow and orange with to give an overall effective color of peach with a bright yellow crest with the overall flower color becoming more yellow as they age and its re-blooming habit; blooming in spring and re-blooming in fall.

2 Drawing Sheets

Botanical classification: *Antirrhinum majus.*
Cultivar designation: 'Snap Daddy Peach'.

CROSS REFERENCE TO A RELATED APPLICATION

This application is related to a U.S. Plant Patent Application filed for a plant derived from the same breeding program that are entitled *Antirrhinum* Plant Named 'Snap Daddy Yellow' (U.S. Plant Pat. No. 21,845) and *Antirrhinum* Plant Named 'Snap Daddy Pink' (U.S. Plant Pat. No. 24,000).

BACKGROUND OF THE INVENTION

The present invention relates to a new and distinct cultivar of *Antirrhinum majus*, and will be referred to hereafter by its cultivar name, 'Snap Daddy Peach'. The new cultivar represents a new snapdragon, a half-hardy perennial grown as an annual in containers and garden beds.

'Snap Daddy Peach' arose as a naturally occurring meristematic mutation of a plant that was growing in a container derived from seed of *Antirrhinum majus* seed strain Liberty Classic Bronze (not patented) during bedding plant production at the Inventor's nursery in Alpharetta, Ga. 'Snap Daddy Peach' was selected as a single unique plant in Fall of 2011 after stable foliage variegation was obtained through multiple rounds of propagation by stem tip cuttings.

Asexual propagation of the new cultivar was first accomplished by stem cuttings in November of 2011 in Alpharetta, Ga. under the direction of the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar as grown in Alpharetta, Ga. These attributes in combination distinguish 'Snap Daddy Peach' as a unique cultivar of *Antirrhinum.*

1. 'Snap Daddy Peach' exhibits variegated foliage with distinct yellow margins and soft, grey-green centers.
2. 'Snap Daddy Peach' exhibits new foliage with margins that are a brighter yellow than the mature foliage.
3. 'Snap Daddy Peach' exhibits full flower heads.
4. 'Snap Daddy Peach' exhibits uniquely colored flowers that are a blend of pink, yellow and orange with to give an overall effective color of peach with a bright yellow crest with the overall flower color becoming more yellow as they age.
5. 'Snap Daddy Peach' blooms in spring and re-blooms in fall.

The parent plant of 'Snap Daddy Peach', a seedling of the seed strain Liberty Classic Bronze, differs from 'Snap Daddy Peach' in having non-variegated foliage that is green in color and in having slightly wider foliage. 'Snap Daddy Peach' can be most closely compared to the cultivars 'Snap Daddy Yellow' and 'Snap Daddy Pink'. Both are similar to 'Snap Daddy Peach' in having variegated foliage. 'Snap Daddy Yellow' differs from 'Snap Daddy Peach' in having foliage margins that are creamy white in color and in having flowers that are yellow in color. 'Snap Daddy Pink' differs from 'Snap Daddy Peach' in having flowers that are pink in color.

BRIEF DESCRIPTION OF THE DRAWINGS

The accompanying colored photographs illustrate the overall appearance and distinct characteristics of the new *Antirrhinnum*. The photographs were taken of plants about 4 months in age as grown in a greenhouse in one-gallon containers in Alpharetta, Ga.

The photograph in FIG. 1 provides a side view of 'Snap Daddy Peach' in bloom.

Figure 1:
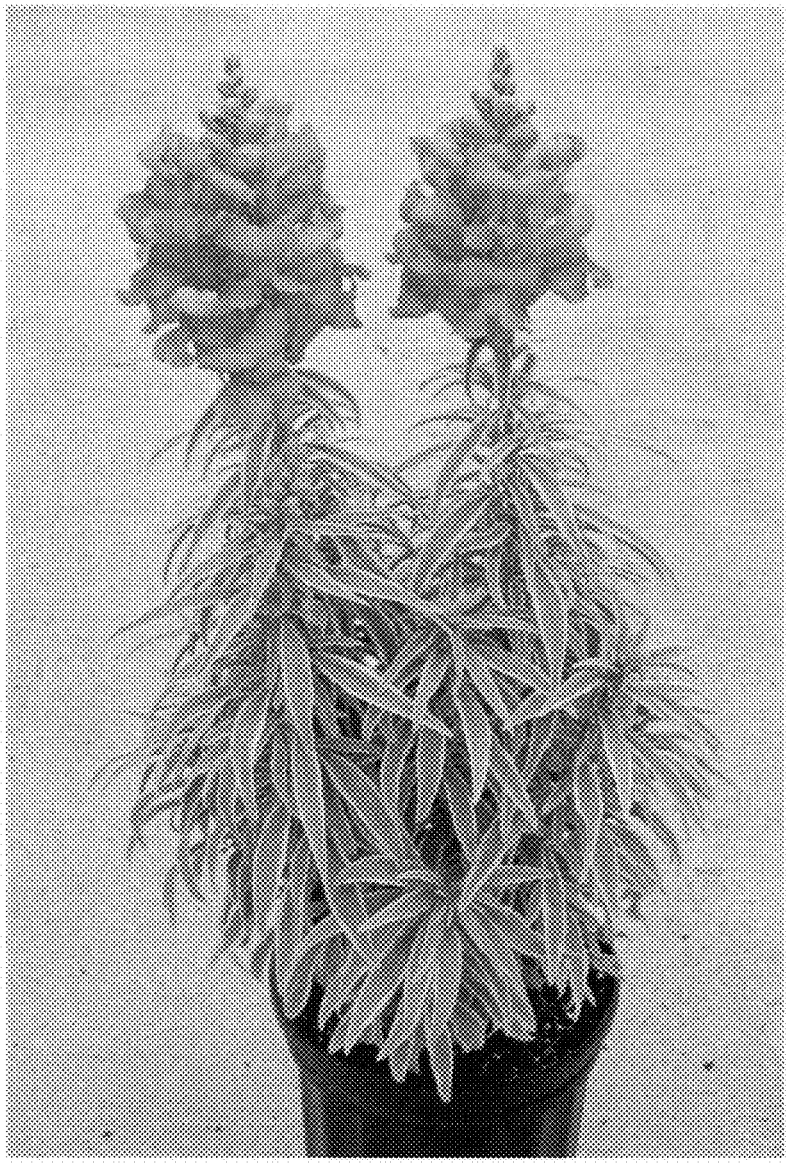
Figure 2:
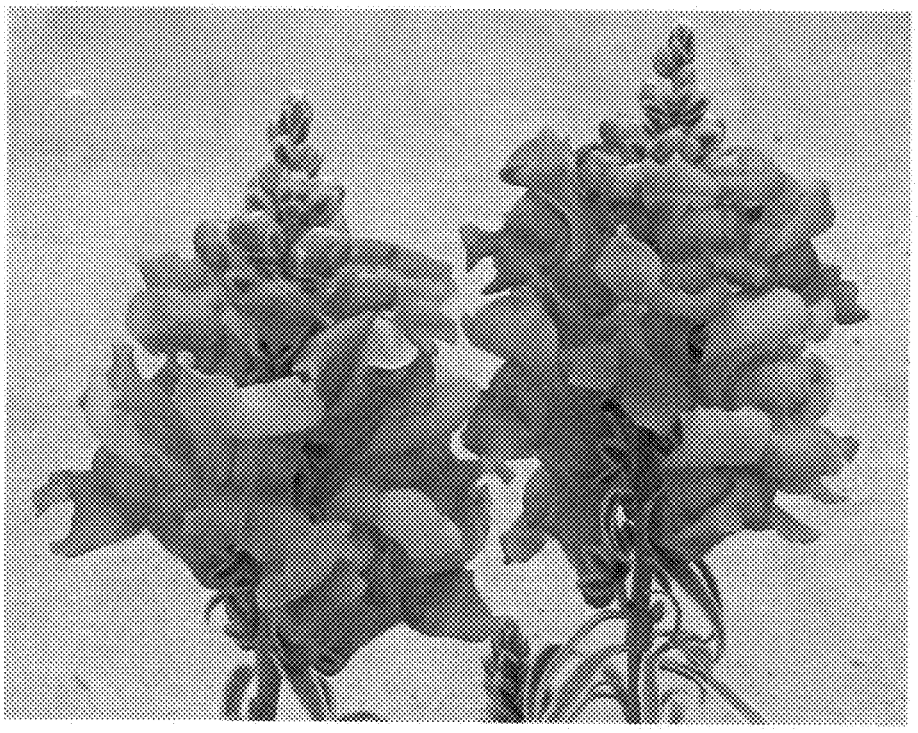

The photograph in FIG. 2 provides a close-up view of the inflorescences of 'Snap Daddy Peach'.

The colors in the photographs may differ slightly from the color values cited in the detailed botanical description, which accurately describe the colors of the new *Antirrhinum*.

DETAILED BOTANICAL DESCRIPTION OF THE PLANT

The following is a detailed description of plants about 4 months in age as grown in a greenhouse in one-gallon containers in Alpharetta, Ga. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—April to June and October to November in Georgia.

*Plant type*.—Half-hardy herbaceous perennial typically grown as an annual.

*Plant habit*.—Upright, dense.

*Height and spread*.—Reaches 30 to 38 cm in height and 20 to 25 cm in width.

*Cold hardiness*.—U.S.D.A. Zone 7.

*Diseases and pests*.—No susceptibility to diseases or pests has been observed.

*Root description*.—Fibrous.

*Propagation*.—Stem cuttings.

*Growth rate*.—Moderate to vigorous.

Stem description:

*Branch habit*.—An average of 10 basal branches in a one-gallon container.

*Stem size*.—An average of 30 cm (including peduncle) in length and 4 mm in width.

*Stem shape*.—Oval.

*Stem color*.—A blend of 145B and 138C.

*Stem surface*.—Puberulent.

*Stem aspect*.—Upright, strong.

*Internode length*.—Up to 7 mm, densely foliaged.

Foliage description:

*Leaf shape*.—Narrowly lanceolate.

*Leaf division*.—Simple with numerous leaves of various sizes from the same node.

*Leaf base*.—Attenuate.

*Leaf apex*.—Narrowly acute.

*Leaf size*.—Up to 7 cm in length and 1.2 cm in width.

*Leaf venation*.—Pinnate, midrib recessed on upper surface, color on upper and lower surface matches leaf.

*Leaf margins*.—Entire.

*Leaf attachment*.—Sessile.

*Leaf arrangement*.—Whorled.

*Leaf surface*.—Dull and very finely puberulent on upper and lower surface.

*Leaf variegation pattern*.—Distinct yellow margins an average of 1.6 mm in width with grey-green centers.

*Leaf color*.—Newly emerged (growth tips) upper and lower surface; centers 144C, margins; 4B, mature upper surface; centers 189A, margins 4D, mature lower surface; centers 191B, margins 10B.

*Leaf number*.—Dense, an average of 30 mature leaves per lateral branch 9 cm in length.

*Leaf aspect*.—Cascading downward from stem.

Flower description:

*Inflorescence type*.—Terminal racemes of bilabiate, blooms from the base to the apex.

*Inflorescence size*.—Average of 12 cm in length and 8 cm in width.

*Lastingness of flower*.—About 5 days, not persistent.

*Flower size*.—About 5 cm in depth and about 4.5 cm in diameter.

*Flower fragrance*.—Very faint.

*Flower number per inflorescence*.—Full heads, an average of 30 per stem in the winter when grown in a single poly greenhouse under natural light.

*Peduncle*.—Oval in shape, up to 12 cm in length and an average of 4.5 mm in width, a blend of 145B and 138C in color, surface is finely puberulent, flower internode length is an average of 6 mm.

*Pedicel*.—About 7 mm in length, about 2 mm in width, oval in shape, color is a blend of 145B and 138C in color, surface is pubescent with glandular hairs, one leaf at base; up to 5 cm in length and 1.1 cm in width with similar characteristics to stem leaves.

*Flower buds*.—Kidney-obovate in shape, about 2.7 cm in length and 1.3 cm in width, color of petal portion is a blend of 64C and 64D at base and apex with center portion 157A and calyx portion the same coloration as open flowers.

*Flower type*.—Bilabiate, held at about a 45° angle to peduncle.

*Calyx*.—Campanulate, about 1 cm in length and 1.7 cm in diameter, persistent.

*Sepals*.—5, fused at base only, elliptic in shape, 5 mm in width and 1 cm in length broadly acute apex, margins entire, variegated with centers 138A in color and margins 158A in color, outer surface highly pubescent with glandular hairs, inner surface is pubescent.

*Corolla features*.—Bilabiate and fused to tube, upper lip; comprised of 2 kidney-shaped lobes that are cupped upwards, each lobe is about 2.2 cm in width and 3 cm in length with rounded and wavy apex, lower lip; comprised of a 2 lobe banner and a raised center lobe with keel and crested interior, combined an average of 2.5 cm in width and 2.5 cm in depth, lower surface of both lips sparsely pubescent and upper surface is glabrous, margins of both lips are entire and slightly ruffled, tube is about 3 cm in length and 1.5 cm in width, color of outer surface of upper and lower lip and outer surface of tube is a blend of 64C, 64D, and 158D, color of inner surface of lower lip is 33A, color of inner surface of upper lip is 33A blending with 64D and 64C and 158D on lower portion, color of inner surface of tube color is NN155D suffused with 64D with the crested region that extends into tube 7A, on mature flowers the 158D color on all lips and surfaces becomes more prominent.

*Receptacle*.—Disk-shaped, gelatinous, 144C in color, about 2.5 mm in diameter and 1.5 mm in depth.

Reproductive organs:

*Gynoecium*.—1 Pistil, about 1.7 cm in length, style is a blend of 145D and 63D in color and 1.6 cm in length and 1 mm in width, stigma expanded club-shape at terminus and about 145D in color, ovary is superior, conical in shape, 144D in color, 3 mm in length and width.

*Androcoecium*.—4 stamens and 4 petaloid stamens, not united, stamens; about 2.3 cm in length; filament is 2 cm in length, 1 mm in width and NN155A in color; anther is amorphously shaped, about 2 mm in length and 1 mm in width and 15A in color, pollen is moderate in quantity and 15A in color, petaloid stamens; 3 cm in length, 2 mm in width with petal like apex about 7 mm in length and 3 mm in width, color of lower linear portion is a blend of 63C and 158D and the petaloid portion is a blend of 34A and 7A.

*Fruit and seed*.—Fruit; a capsule, oblong in shape with a long thin beak, an average of 1.5 cm in length (including beak 6 mm in length and 1 mm in width), color is a blend of N199D and 200A, seeds; round, spiky, about 1.2 mm in diameter, 200B in color.

It is claimed:

1. A new and distinct cultivar of *Antirrhinum* plant named 'Snap Daddy Peach' as herein illustrated and described.

* * * * *